United States Patent [19]

Miller et al.

[11] Patent Number: 4,840,017
[45] Date of Patent: Jun. 20, 1989

[54] METHOD FOR FILLING COLLAPSIBLE CONTAINERS

[75] Inventors: Robert A. Miller, Crystal Lake; Albert L. Stone, Buffalo Grove, both of Ill.

[73] Assignee: Baxter Healthcare Corporation, Deerfield, Ill.

[21] Appl. No.: 80,853

[22] Filed: Aug. 3, 1987

[51] Int. Cl.⁴ .......................... B65B 3/04; B65B 7/14; B65B 51/10
[52] U.S. Cl. ...................... 53/468; 53/469; 53/471; 53/479
[58] Field of Search ............... 53/268, 281, 434, 468, 53/469, 471, 477, 479, 512; 206/438, 484, 806; 383/9, 10, 26, 28, 66; 604/408, 410, 411, 415

[56] References Cited

U.S. PATENT DOCUMENTS

| | | | |
|---|---|---|---|
| 3,299,603 | 1/1967 | Shaw | 53/426 |
| 3,514,919 | 6/1970 | Ashton et al. | 53/469 X |
| 3,554,256 | 11/1968 | Anderson. | |
| 4,072,233 | 2/1978 | Kramer. | |
| 4,360,996 | 11/1982 | Rutter | 53/268 X |
| 4,519,184 | 5/1985 | Brunswick | 53/268 X |
| 4,524,563 | 6/1985 | Sassi | 53/268 X |
| 4,534,154 | 8/1985 | Gaubert | 53/268 X |
| 4,598,529 | 7/1986 | Pongrass et al. | 53/468 X |
| 4,723,956 | 2/1988 | Schnell et al. | 604/408 X |

OTHER PUBLICATIONS

I. M. Anderson, Intasept-Aseptic Integrity in Bag-in-Box Packaging from "Food Technology in Australia", vol. 37(9), Sep. 1985, pp. 399, 400, 401.

Primary Examiner—Robert L. Spruill
Assistant Examiner—Ann Tran
Attorney, Agent, or Firm—Kay H. Pierce; Paul Flattery; Bradford Price

[57] ABSTRACT

A flexible collapsible container is filled with fluid by connecting a fluid conduit to a tubular port which communicates through one of the walls of the container to the container interior, and rupturing a sealing diaphragm that closes the bore of the tubular port. One then passes fluid through the conduit to fill the container. Thereafter, one seals either or both the tubular port and plastic wall which carries it to the other, opposed plastic wall of the container with seal line means to close off flow communication between the bore of the tubular port and a major portion of the container interior which contains the fluid. The effect of this is to block flow communication between the bore and the fluid so that the contents of the container remain sealed on disengagement of the fluid conduit from the tubular port.

6 Claims, 1 Drawing Sheet

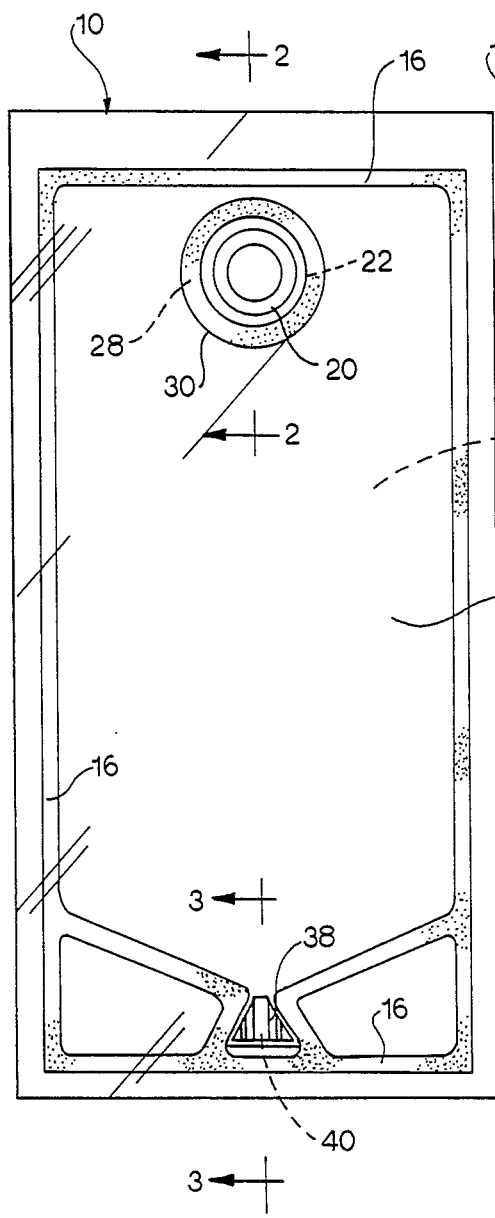
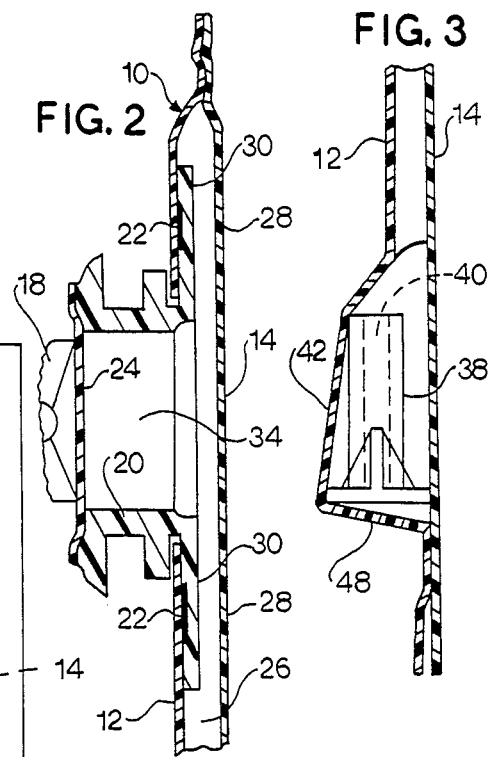
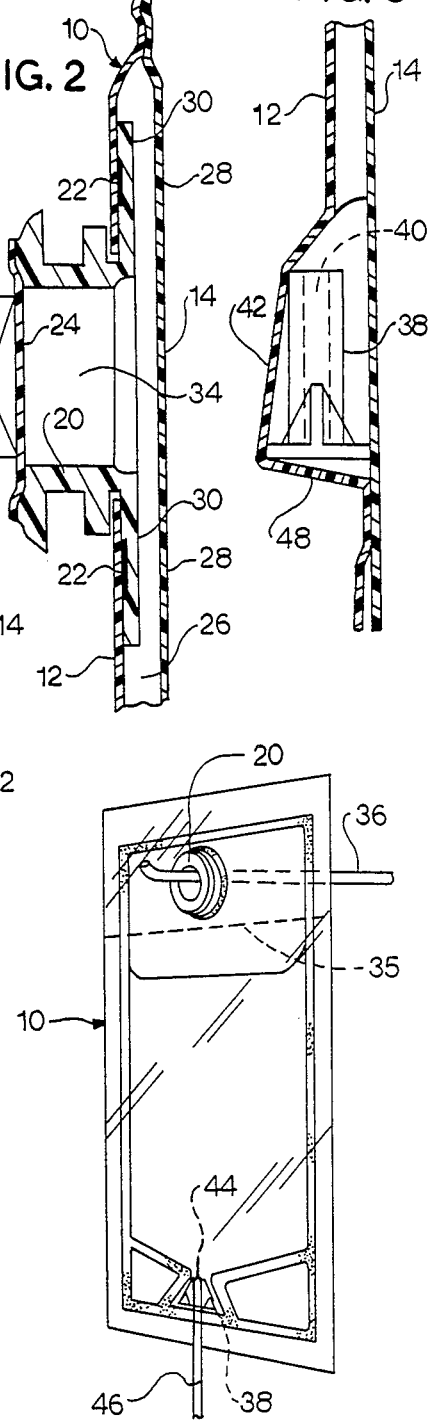

METHOD FOR FILLING COLLAPSIBLE CONTAINERS

TECHNICAL FIELD

In the field of parenteral solutions, and also enteral liquid nutrients, there is a demonstrated need for containers that may be manufactured and filled under sterile conditions at reduced cost. Additionally, the containers must also be entirely convenient and effective in their end use, and they must be strong and safe.

In the article by I.M. Anderson entitled Intasept - Aseptic Integrity in Bag-In-Box Packaging, Food Technology in Australia, vol. 37 (9) September, 1985, pp. 399-401 a system is demonstrated for bag-in box packaging of liquids, and a machine for aseptic filling of such flexible, collapsible containers. As described in the article, a flexible, collapsible container which comprises a pair of flexible plastic walls peripherally joined together is filled through the use of a tubular port which extends through one of the walls of the container to the container interior, and which carries spaced, outer and inner sealing diaphragms at either end of the tubular port. The outer diaphragm is outside of the walls of the container, and the inner diaphragm is inside of the walls thereof.

The outer diaphragm is completely sealed to the tubular port about its periphery, but the inner diaphragm is only spot sealed about its periphery so that fluid flow can take place across the inner diaphragm between the spot seals.

As described in the article, the flexible, collapsible container is connected to the Intasept filling machine. The outside of the tubular port is sterilized, and the container interior is typically already sterile. After sterilization, the outer membrane is penetrated, but not the inner membrane. The container is then filled through the tubular port with the desired amount of liquid, following which the inner membrane is welded in a continuous loop seal by welding which takes place through both walls of the container so that the container interior is sealed.

This bag system and the method for filling and sealing it has certain disadvantages. For example, a special laminated material must be used for the inner membrane, so that the inner membrane can be heat sealed to the tubular port, while the opposite container wall, through which the heat sealing process takes place, does not seal to the inner membrane. Additionally, the initial attachment of the intermittently sealed inner membrane is a matter of some complexity in the first place. Accordingly, the structure described in the Anderson article is difficult to make and costly.

In accordance with this invention, a flexible, collapsible container is provided which may be filled with conventional, aseptic filling machines such as the Intasept machine, but which is a simpler structure, and which may be processed in a simpler manner to achieve the desired results of an aseptically sealed container for liquid materials with an improved seal. The liquid materials placed in the container may typically be parenteral solutions or liquid enteral preparations for medical usage, but there is no limitation on the types of fluids that may be stored in such a container. Food such as milk may be so stored, or biological preparations, bacteria cultures, or any other desired fluid.

DESCRIPTION OF THE INVENTION

In this invention, one fills with fluid a flexible, collapsible container which comprises a pair of flexible plastic walls peripherally joined together. To accomplish this, one connects a fluid conduit to a tubular port which communicates through one of the plastic walls to the container interior, rupturing a sealed diaphragm that closes the bore of the tubular port, typically in the connecting process. One then passes fluid through the conduit to fill the container, followed by sealing at least one of the tubular port and one plastic wall to the other plastic wall, forming a seal line that serves to close off flow communication between the tubular port and the portion of the container interior that contains the fluid. Thus the container is sealed.

Following this, one may, as an added, subsequent step, cut away at least a portion of the other plastic wall situated in registry with the bore of the tubular port, to provide a hanger port that extends through the container. Typically, the remnants of the sealing diaphragm may be removed as well.

It may be desirable for the seal line described above to be a closed-loop seal line that completely surrounds the bore, to effectively block flow communications between the bore and the rest of the container interior.

It can be seen that the formation of this seal line is any easy matter of conventional heat sealing, forming the seal between either or both the tubular port and wall which carries it, and the other wall of the container, without any critical technical problems that are caused by the presence of a laminated, inner membrane or diaphragm which has been previously spot welded to the tubular port, as in the system of the Anderson article described above. Thus this present system, which preferably utilizes only a single sealing diaphragm, exhibits significant manufacturing and functioning advantages, particularly an improved quality seal.

The container of this invention may then carry separate means for obtaining access to its contents, using an access device that is known to the art.

DESCRIPTION OF DRAWINGS

In the drawings, FIG. 1 is a plan view of a flexible, collapsible container in accordance with this invention, shown in its sealed configuration.

FIG. 2 is a sectional view taken along line 2—2 of FIG. 1, showing the same container in a step of its filling process.

FIG. 3 is a sectional view taken along line 3—3 of FIG. 1.

FIG. 4 is a perspective view of the filled container of this invention, shown in hanging relation and with the contents being removed by a conventional, tubular set.

DESCRIPTION OF SPECIFIC EMBODIMENTS

Referring to the drawings, flexible, collapsible container 10 comprises a pair of plastic walls 12, 14 which are joined together by conventional, peripheral heat seal lines 16 so that container 10 has a sealed interior. The material of walls 12, 14 may be of a wide range of heat sealable plastic sheeting, for example, polyethylene, polypropylene, or the like. Plastic walls 12 and/or 14 may incorporate a barrier material such as aluminum foil, metallized polyester, ethylene vinyl alcohol, or polyvinylidine chloride, if desired, to further reduce oxygen and water vapor transfer.

Container 10 may be manufactured by a thermoforming process, if desired, or it may be simply manufactured by the heat sealing of a pair of plastic sheets, 12, 14 together.

In accordance with this invention, one may connect a fluid conduit coupler 18 to tubular port 20. Coupler 18 communicates with the desired fluid supply, which is typically in a known aseptic filling machine such as the Intasept aseptic bag-in-box filler. Tubular port 20 is shown to be heat sealed along annular seal line 22 to bag wall 12. In the process of such connection, after the stage shown in FIG. 2 and a step of sterilizing the outer surface of sealing diaphragm 24, diaphragm 24 may be ruptured so that a flow path is provided between the material to be filled within the filling machine and the interior 26 of container 10.

Accordingly, fluid is passed into the container through tubular port 20 until container 10 is filled.

Following this, prior to disconnecting coupler 18, one may provide another heat seal between annular flange 30 of tubular port 20 and the other wall 14 of container 10, at location 28 (FIG. 2) to form an annular seal that blocks flow communication between bore 34 of tubular port 20 and the majority of the interior volume 26 of container 10. By this means, the fluid present in the interior of container 10 may be sealed under aseptic conditions. Following this, coupler 18 of the filling machine may be disconnected, and container 10 may be removed to make room for the next container for filling within the filling machine.

Alternatively, seal line 28 may be replaced with transverse seal line 35 (FIG. 4), which extends completely across bag 10 to isolate port 20 from the majority of the interior volume of the bag and from the fluid carried therein.

If desired, the remnants of sealing diaphragm 24, and a portion of bag wall 14 which is within registry with bore 34 and within the new annular seal at area 28, may be removed, so that bag 10 may be placed upon a hanger 36 for vertical suspension as the contents of bag 10 are delivered.

Means are provided for obtaining access to the interior of container 10. Specifically, port member 38, defining aperture 40, is shown to be captured in a chamber 42 defined between container walls 12, 14. A spike 44 of a conventional parenteral or enteral solution administration set 46 may penetrate portion 48 of bag wall 12 to enter bore 40 of member 38, this structure, and the function thereof, being described in the copending patent application of William J. Schnell et al., Ser. No. 650,400, filed Sept. 14, 1984 and entitled Port Free Container now abandoned in view of continuation application Ser. No. 905,738 filed Sept. 10, 1986, and issued on Feb. 9, 1988, as U.S. Pat. No. 4,723,956.

Accordingly, by this invention, a simplified container is provided which is capable of sterile filling, in which the sterile fill port, after use, is turned into a hanger hole while the contents of the container are retained in sealed, aseptic condition. For use, the bag may be penetrated with a conventional spike of a parenteral or enteral solution set for access to the contents in a conventional manner.

If desired, a bubble of inert gas such as nitrogen or argon may be added to container 10 on filling to provide an oxygen-free gas bubble to the contents. This facilitates the measurement of the volume of contents dispensed while keeping the container free from oxygen.

The above has been offered for illustrative purposes only, and is not intended to limit the scope of the invention of this application, which is as defined in the claims below.

That which is claimed is:

1. The method of filling with fluid a flexible, collapsible container which comprises a pair of flexible plastic walls peripherally joined together, which method comprises:

connecting a fluid conduit to a tubular port which communicates through one of said walls to the container interior, and rupturing a sealing diaphragm that closes the bore of said tubular port; passing fluid through said conduit to fill said container;

sealing at least one of said tubular port and one plastic wall to the other plastic wall with a closed-loop seal line that completely surrounds said bore, to block flow communication between said bore and most of the container interior, whereby the contents of said container remain sealed on disengagement of said fluid conduit from the tubular port; and cutting away at least portions of said other plastic wall situated in registry with said closed-loop seal line, whereby the resulting open port extending through said tubular port and container can serve as a hanger port.

2. The method of claim 1 in which said tubular port carries only a single sealing diaphragm.

3. The method of claim 2 in which said container carries separate means for obtaining access to its contents.

4. The method of claim 1 in which said filling takes place under sterile conditions.

5. The method of filling with fluid a flexible, collapsible container which comprises a pair of flexible plastic walls peripherally joined together, which method comprises:

connecting a fluid to a tubular port which communicates through one of said walls to the container interior, and rupturing a sealing diaphragm that closes the bore of said tubular port, said tubular port carrying only a single sealing diaphragm;

passing fluid through said conduit to fill said container;

sealing at least one of said tubular portions and one plastic wall to the other plastic wall with a closed-loop seal line that completely surrounds said bore, to block flow communication between said bore and most of the container interior, whereby the contents of said container remain sealed on disengagement of said fluid conduit from the tubular port;

thereafter making connection with a tubular flow set with separate means carried on said container for obtaining access to its contents, for draining the contents from the container; and cutting away at least portion of said plastic wall situated in registry with said closed-loop seal line, whereby the resulting open port extending through said tubular port and container can serve as a hanger port.

6. The method of claim 5 in which said filling takes place under sterile conditions.

* * * * *